United States Patent
Chen et al.

(10) Patent No.: US 11,970,569 B2
(45) Date of Patent: *Apr. 30, 2024

(54) POLYURETHANE FOAM SPONGE AND WOUND DRESSING HAVING THE SAME

(71) Applicant: Tronjen Medical Technology Inc., Taichung (TW)

(72) Inventors: Szu-Hsien Chen, Taichung (TW); Ya-Wen Ku, Taichung (TW); Ren-Shian Wang, Taichung (TW); Chiu-Fang Chen, Taichung (TW)

(73) Assignee: Tronjen Medical Technology Inc., Taichung (TW)

( * ) Notice: Subject to any disclaimer, the term of this patent is extended or adjusted under 35 U.S.C. 154(b) by 671 days.

This patent is subject to a terminal disclaimer.

(21) Appl. No.: 17/021,794

(22) Filed: Sep. 15, 2020

(65) Prior Publication Data

US 2021/0395438 A1 Dec. 23, 2021

(30) Foreign Application Priority Data

Jun. 22, 2020 (TW) ................................ 109121108

(51) Int. Cl.
| | | |
|---|---|---|
| *A61F 13/00* | (2006.01) | |
| *B32B 7/12* | (2006.01) | |
| *B32B 27/06* | (2006.01) | |
| *B32B 27/40* | (2006.01) | |
| *C08G 18/08* | (2006.01) | |
| *C08G 18/10* | (2006.01) | |
| *C08G 18/20* | (2006.01) | |
| *C08G 18/24* | (2006.01) | |
| *C08G 18/30* | (2006.01) | |
| *C08G 18/32* | (2006.01) | |
| *C08G 18/48* | (2006.01) | |
| *C08G 18/66* | (2006.01) | |
| *C08G 18/73* | (2006.01) | |
| *A61F 13/53* | (2006.01) | |

(52) U.S. Cl.
CPC .............. *C08G 18/73* (2013.01); *A61F 13/00* (2013.01); *B32B 7/12* (2013.01); *B32B 27/065* (2013.01); *B32B 27/40* (2013.01); *C08G 18/10* (2013.01); *C08G 18/14* (2013.01); *C08G 18/2063* (2013.01); *C08G 18/244* (2013.01); *C08G 18/302* (2013.01); *C08G 18/3206* (2013.01); *C08G 18/4829* (2013.01); *C08G 18/4833* (2013.01); *C08G 18/6677* (2013.01); *C08G 18/6692* (2013.01); *A61F 2013/00336* (2013.01); *A61F 2013/00659* (2013.01); *A61F 2013/00855* (2013.01); *A61F 2013/530802* (2013.01); *B32B 2266/0278* (2013.01); *B32B 2307/724* (2013.01); *B32B 2307/7265* (2013.01); *B32B 2535/00* (2013.01); *C08G 2110/0083* (2021.01)

(58) Field of Classification Search
CPC . A61F 13/00; C08G 18/4829; C08G 18/4833; C08G 18/6677; C08G 18/6692; C08G 18/73
See application file for complete search history.

(56) References Cited

U.S. PATENT DOCUMENTS

| | | | |
|---|---|---|---|
| 4,789,720 | A | 12/1988 | Teffenhart |
| 5,064,653 | A | 11/1991 | Sessions et al. |
| 5,719,201 | A | 2/1998 | Wilson |
| 9,168,324 | B2 | 10/2015 | Mager et al. |
| 2014/0255373 | A1 | 9/2014 | Schonberger |
| 2020/0093953 | A1 | 3/2020 | Kim et al. |
| 2021/0023256 | A1* | 1/2021 | Hsiao ...................... A61L 15/60 |
| 2021/0023814 | A1* | 1/2021 | Chen ...................... B32B 5/022 |

FOREIGN PATENT DOCUMENTS

| | | |
|---|---|---|
| CN | 1037523 | 11/1989 |
| CN | 102573933 | 7/2012 |
| CN | 101687058 | 6/2016 |
| CN | 106137539 | 11/2016 |
| CN | 109276739 | 1/2019 |
| EP | 3106181 | 12/2016 |
| GB | 2362651 | 11/2001 |
| TW | 200936625 | 9/2009 |

OTHER PUBLICATIONS

Office Action in Taiwanese Appln. No. 109121108, dated Apr. 30, 2021, 12 pages (with English Machine Translation).
Huang, "Study on a New Type of Composite Hydrophilic Polyurethane Wound Dressing," Sichuan University, 2001, Dissertation, (abstract only).
Office Action in Chinese Appln. No. 202110211968.9, dated Sep. 2, 2022, 15 pages (with English Translation).
Li et al., "Application of Hydrophilic Polyurethane in Medical Dressing," Chemical Propellants and Polymeric Materials, Sep. 2009, 5:22-25, 37 (with machine translation).

* cited by examiner

*Primary Examiner* — Michael L Leonard
(74) *Attorney, Agent, or Firm* — Fish & Richardson P.C.

(57) ABSTRACT

Disclosed herein is a polyurethane foam sponge produced by the steps of a) providing an hydrophobic polyol which has six hydroxyl groups, b) providing a hydrophilic diisocyanate obtained by reacting a diisocyanate with a hydrophilic polyether diol, c) reacting the hydrophobic polyol with the hydrophilic diisocyanate to obtain a prepolymer which includes 3 to 6 isocyanate groups, and d) mixing the prepolymer with a hydrophilic polyether polyol, a blowing agent, an end-capping agent, a reinforcing agent, and a catalyst to obtain the polyurethane foam sponge. A wound dressing including the polyurethane foam sponge is also disclosed.

13 Claims, No Drawings

POLYURETHANE FOAM SPONGE AND WOUND DRESSING HAVING THE SAME

CROSS-REFERENCE TO RELATED APPLICATION

This application claims priority of Taiwanese Invention Patent Application No. 109121108, filed on Jun. 22, 2020.

FIELD

The disclosure relates to a polyurethane foam sponge and a wound dressing having the same. In particular, the wound dressing is suitable for contact with open wounds, facilitating optimal wound healing.

BACKGROUND

Wound dressings have been used to promote healing, to protect damaged tissues from contamination by dirt and foreign substances, and to protect against infection. Self-adherent silicone foam dressings and polyurethane (PU) dressings are the most commonly used dressings in wound care. However, the self-adherent silicone foam dressings and PU dressings have low vapor permeability and may cause wound infiltration and allergy, and thus frequent replacement of such wound dressings and wound debridement are required.

SUMMARY

Accordingly, in a first aspect, the present disclosure provides a polyurethane foam sponge produced by the steps of:
a) providing a hydrophobic polyol which has six hydroxyl groups, and which is obtained by:
  a-1) reacting a branched triol with a first diisocyanate to obtain a triisocyanate intermediate, and
  a-2) reacting the triisocyanate intermediate with a hydrophobic polyether triol;
b) providing a hydrophilic diisocyanate obtained by reacting a second diisocyanate with a hydrophilic polyether diol;
c) reacting the hydrophobic polyol with the hydrophilic diisocyanate to obtain a prepolymer which includes 3 to 6 isocyanate groups; and
d) mixing the prepolymer with a hydrophilic polyether polyol, a blowing agent, an end-capping agent, a reinforcing agent, and a catalyst to obtain the polyurethane foam sponge.

In a second aspect, the present disclosure provides a wound dressing, including:
a waterproof and vapor-permeable carrier sheet;
an adhesive layer disposed on the carrier sheet; and
a polyurethane foam sponge as described above, the polyurethane foam sponge being disposed on the adhesive layer opposite to the carrier sheet.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The present disclosure provides a polyurethane foam sponge produced by the steps of:
a) providing a hydrophobic polyol which has six hydroxyl groups, and which is obtained by:
  a-1) reacting a branched triol with a first diisocyanate to obtain a triisocyanate intermediate, and
  a-2) reacting the triisocyanate intermediate with a hydrophobic polyether triol;
b) providing a hydrophilic diisocyanate obtained by reacting a second diisocyanate with a hydrophilic polyether diol;
c) reacting the hydrophobic polyol with the hydrophilic diisocyanate to obtain a prepolymer which includes 3 to 6 isocyanate groups; and
d) mixing the prepolymer with a hydrophilic polyether polyol, a blowing agent, an end-capping agent, a reinforcing agent, and a catalyst to obtain the polyurethane foam sponge.

According to the present disclosure, the branched triol is selected from the group consisting of 1,1,1-trimethylolpropane (TMP), triethanolamine, glycerol, 1,2,6-hexanetriol, 1,2,4-butanetriol, glycerol ethoxylate, and combinations thereof.

According to the present disclosure, the first diisocyanate and the second diisocyanate are independently selected from the group consisting of hexamethylene diisocyanate (HDI), methylene dicyclohexyl diisocyanate (H12MDI), isophorone diisocyanate (IPDI), and combinations thereof.

According to the present disclosure, the hydrophobic polyether triol is selected from the group consisting of poly(propylene glycol) triol, poly(tetramethylene ether) glycol triol, and a combination thereof.

According to the present disclosure, the hydrophilic polyether diol is polyethylene glycol (PEG).

According to the present disclosure, the hydrophilic polyether polyol may be polyethylene glycol having a weight-average molecular weight ranging from 400 g/mol to 2,000 g/mol. In certain embodiments, the hydrophilic polyether polyol is polyethylene glycol having a weight-average molecular weight ranging from 600 g/mol to 1,000 g/mol.

According to the present disclosure, the blowing agent is selected from the group consisting of water and sodium bicarbonate.

According to the present disclosure, the end-capping agent is a silane-containing compound.

According to the present disclosure, the silane-containing compound is an aminosilane compound selected from the group consisting of aminoalkyl alkoxysilane, aminoalkyl trialkylsilane, and a combination thereof.

In certain embodiments, the aminosilane compound is selected from the group consisting of (3-aminopropyl)triethoxysilane (APTES), (3-aminopropyl)trimethoxysilane (APTMS), (3-aminopropyl)diethoxymethylsilane (APDEMS), and combinations thereof.

According to the present disclosure, the reinforcing agent is polysiloxane.

The present disclosure also provides a wound dressing, including:

a waterproof and vapor-permeable carrier sheet;
an adhesive layer disposed on the carrier sheet; and
a polyurethane foam sponge as described above, the polyurethane foam sponge being disposed on the adhesive layer opposite to the carrier sheet.

According to the present disclosure, the carrier sheet is made of polyurethane, and the adhesive layer is a polyurethane adhesive layer.

According to the present disclosure, the wound dressing has a thickness ranging from 1 mm to 5 mm.

The applicants have observed, via a microscopic scale measurement or a mesoscopic scale measurement, that the hydrophobic region, which is formed by the hydrophobic polyol and is located at the inside of the prepolymer, and the hydrophilic region, which is formed by the hydrophilic diisocyanate and is located at the outside of the prepolymer, are in a state of phase separation. This property causes the polyurethane foam sponge to be in a state of microphase separation, thereby facilitating the formation of tiny holes through which water vapor can penetrate.

The disclosure will be further described by way of the following examples. However, it should be understood that the following examples are solely intended for the purpose of illustration and should not be construed as limiting the disclosure in practice.

EXAMPLES

Example 1. Preparation of Polyurethane Foam Sponge of Present Disclosure

An exemplary polyurethane (PU) foam sponge of the present disclosure was prepared as follows and later used to prepare an exemplary wound dressing of the present disclosure.

In step (a1), 1,1,1-trimethylolpropane (TMP) and hexamethylene diisocyanate (HDI) were mixed in a molar ratio of 1:3, and 0.05 wt % triethylenediamine (TEDA) (based on the total weight of TMP and HDI) was then used as a catalyst. The resultant mixture was stirred at 80° C. for 90 minutes under an enclosed nitrogen atmosphere. During the reaction above, fourier transform-infrared (FT-IR) spectroscopy analysis was conducted to monitor the presence of the characteristic NCO group (-NCO) peak at 2270 $cm^{-1}$. The characteristic NCO group peak at 2270 $cm^{-1}$ was successfully detected, indicating that a triisocyanate intermediate was obtained.

In step (a2), the triisocyanate intermediate and poly (propylene glycol) triol (PPG 4000 triol) were mixed in a molar ratio of 1:3, and 0.05 wt % TEDA (based on the total weight of the triisocyanate intermediate and PPG 4000 triol) was then used as a catalyst. The resultant mixture was stirred at 80° C. for 90 minutes under an enclosed nitrogen atmosphere. During the reaction above, FT-IR spectroscopy analysis was performed as described in step (a1). The characteristic NCO group peak at 2270 $cm^{-1}$ was not detected, indicating that a hydrophobic polyol which had six hydroxyl groups was obtained.

In step (b), poly(ethylene glycol) diol (PEG 1000 diol) and HDI were mixed in a molar ratio of 1:2, and 0.05 wt % TEDA (based on the total weight of PEG 1000 diol and HDI) was then used as a catalyst. The resultant mixture was stirred at 80° C. for 90 minutes under an enclosed nitrogen atmosphere. During the reaction above, FT-IR spectroscopy analysis was performed as described in step (a1). The characteristic NCO group peak at 2270 $cm^{-1}$ was successfully detected, indicating that a hydrophilic diisocyanate was obtained.

In step (c), the hydrophobic polyol and the hydrophilic diisocyanate were mixed in a molar ratio of 1:6, followed by stirring at 80° C. for 90 minutes under an enclosed nitrogen atmosphere. During the reaction above, FT-IR spectroscopy analysis was performed as described in step (a1). The characteristic NCO group peak at 2270 $cm^{-1}$ was successfully detected, indicating that a prepolymer which included 6 isocyanate groups was obtained. The prepolymer had a hydrophobic interior and a hydrophilic exterior.

In step (d), the prepolymer, polyethylene glycol (PEG 600), water, (3-aminopropyl)triethoxysilane (APTES), and polydimethylsiloxane (PDMS) (which had a weight-average molecular weight ranging from 1,000 g/mol to 3,000 g/mol) were mixed in a molar ratio of 1:1:0.4:0.3:0.3, and 0.1 wt % of stannous octoate (T9) was then used as a catalyst (based on the total weight of the above-mentioned reactants). The resultant mixture was stirred at 20° C. for 10 seconds to 30 seconds under an enclosed nitrogen atmosphere, so as to obtain a PU intermediate product.

The PU intermediate product thus obtained was coated on a silicon-based release paper, followed by standing at 30° C. for 24 hours, so as to obtain a PU foam sponge having a thickness of 3.5 mm.

Example 2. Preparation of Wound Dressing Patch of Present Disclosure

A PU adhesive (Baymedix®, Covestro AG Co., Ltd.) was coated on a PU film (VPT 9101 T, Covestro AG Co., Ltd.) (which had a thickness of about 25 μm) using the technique well known to and routinely used by one skilled in the art, so that an adhesive layer (which had a thickness of about 20 μm) was formed on the PU film.

Thereafter, the PU intermediate product obtained in Example 1 was coated on the adhesive layer opposite to the PU film, followed by standing at 30° C. for 24 hours, so as to obtain a wound dressing patch having a PU foam sponge (which had a thickness of about 3.5 mm).

Example 3. Evaluation for the Qualities of Wound Dressing Patch and Polyurethane Foam Sponge According to this Disclosure A. Test Samples The test samples used in this example are listed in Table 1.

TABLE 1

| Test sample | Size (width × length × thickness) | Source |
|---|---|---|
| Wound dressing patch of the present disclosure | 10 cm × 10 cm × 3.5 5 mm | Example 2 |
| PU foam sponge of the present disclosure | 10 cm × 10 cm × 3.5 5 mm | Example 1 |
| Self-adherent silicone foam dressing patch (trade name: Mepilex ® 294100) | 10 cm × 10 cm × 4 mm | Mölnlycke Health Care |
| PU dressing patch ( cat. no. P1-014-01-Y) | 10 cm × 10 cm × 3.5 mm | TAICEND Co., Ltd., Taiwan |

B. Measurement of Water Vapor Transmission Rate (WVTR)

The water vapor transmission rate of each test sample was measured according to DIN EN 13726-2 (2002). The experimental data thus obtained are expressed as g/m²/day.

C. Measurement of Water Absorbency

The water absorbency of each test sample was measured according to DIN EN 13726-1 (2002) Part 3.2/3.3.

The water absorbency was calculated using the following Equation (I):

$$A=(B-C)/C \qquad (I)$$

where A=water absorbency
B=weight of respective test sample after the test (g)
C=weight of respective test sample before the test (g)

D. Determination of the Degree of Skin Infiltration

A respective one of the four test samples was applied to the skin surface of the upper arm of a corresponding test human subject. After application for 24 hours, the respective test sample was removed, and the area of skin infiltration of the corresponding test human subject was visually observed and measured.

The degree of skin infiltration (%) was calculated using the following Equation (II):

$$D=(E/F) \times 100 \qquad (II)$$

where D=degree of skin infiltration (%)
E=area of skin infiltration of corresponding test human subject (cm²)
F=area of respective test sample (cm²)

Results:

As shown in Table 2 below, the WVTRs and water absorbencies determined in the wound dressing patch and PU foam sponge of the present disclosure were higher than those determined in the self-adherent silicone foam dressing patch and the PU dressing patch. In addition, the degrees of skin infiltration determined in the wound dressing patch and PU foam sponge of the present disclosure were significantly lower than those determined in the self-adherent silicone foam dressing patch and the PU dressing patch.

These results indicate that the wound dressing patch and PU foam sponge of the present disclosure have good vapor permeability, moisture retention, and water absorbency, and can effectively remove excess wound fluid (i.e., exudate) from the immediate vicinity of the wound and thereby prevent wound infiltration.

TABLE 2

| Test sample | WVTR (g/m²/day) | Water absorbency (g/g) | Degree of skin infiltration (%) |
|---|---|---|---|
| PU foam sponge of the present disclosure | 3500 | 1200 | 0 |
| Wound dressing patch of the present disclosure | 1500 | 1200 | 0 |
| Self-adherent silicone foam dressing patch | 100 | 600 | >90 |
| PU dressing patch | 800 | 1000 | >30 |

Example 4. Wound Healing Assay

A. Test Animals

Nulliparous female Sprague Dawley (S.D.) rats (5-12 weeks old, body weight>120 g) were purchased from Laboratory Animal Center, National Cheng Kung University. The S.D. rats were kept in an animal room with an independent air conditioning system under the following laboratory conditions: a temperature of 22±3° C. and a relative humidity of 30-70%. Furthermore, water and feed were provided ad libitum for all the experimental animals.

B. Test Samples

Pieces of the wound dressing patch of the present disclosure, the self-adherent silicone foam dressing patch, and the PU dressing patch as described in Table 1 were sterilized by gamma rays (35 kGy) and were used for the following experiment.

C. Experimental Procedures

The S.D. rats were divided into 3 groups, including one experimental group and two comparative groups (i.e., comparative groups 1 and 2) (n=12 for each group). The dorsal part of each S.D. rat was shaved and then disinfected with 75% alcohol. Thereafter, the S.D. rats were anesthetized with isoflurane, followed by cutting to form a skin wound having an area of about 2 cm×2 cm on the back of the respective S.D. rat using sterile surgical scissors and a blade.

The skin wounds of the experimental group, the comparative group 1 and the comparative group 2 were respectively applied with the sterilized wound dressing patch of the present disclosure, self-adherent silicone foam dressing patch, and PU dressing patch described in section B of this example, followed by fixing the dressing patches with breathable elastic bandages.

On Day 1, Day 4, and Day 7 after the application of the dressing patches, three S.D. rats were taken from each group and their skin wounds were photographed using a digital camera. Such three rats of each group were then discarded from the experiment. For the other S.D. rats in each group, the respective skin wound was treated with a new piece of the corresponding dressing patch as described above, and the respective wound area was calculated by ImageJ software.

Results:

The wound areas determined in the S.D. rats are shown in Table 3. It can be seen from Table 3 that, on Day 7 after the application of the dressing patches, the wound area of the experimental group was significantly smaller than those of the comparative groups 1 and 2, indicating that the wound dressing patch of the present disclosure can effectively promote wound healing.

TABLE 3

| | Experimental group | Comparative group 1 | Comparative group 2 |
|---|---|---|---|
| | | Wound area (cm²) | |
| Day 1 | 2.89 ± 0.13 | 3.61 ± 0.24 | 3.24 ± 0.23 |
| Day 4 | 1.06 ± 0.16 | 2.53 ± 0.21 | 2.05 ± 0.31 |
| Day 7 | 0.09 ± 0.02 | 0.64 ± 0.03 | 0.35 ± 0.09 |

Summarizing the above test results, it is clear that the wound dressing patch of the present disclosure has satisfactory vapor permeability, moisture retention, and water absorbency, and can effectively remove wound exudate from the wound and thereby prevent wound infiltration. In addition, the wound dressing patch of the present disclosure can effectively promote wound healing.

All patents and references cited in this specification are incorporated herein in their entirety as reference. Where there is conflict, the descriptions in this case, including the definitions, shall prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A polyurethane foam sponge produced by the steps of:
   a) providing a hydrophobic polyol which has six hydroxyl groups, and which is obtained by:
      a-1) reacting a branched triol with a first diisocyanate to obtain a triisocyanate intermediate, and
      a-2) reacting the triisocyanate intermediate with a hydrophobic polyether triol;
   b) providing a hydrophilic diisocyanate obtained by reacting a second diisocyanate with a hydrophilic polyether diol;
   c) reacting the hydrophobic polyol with the hydrophilic diisocyanate to obtain a prepolymer which includes 3 to 6 isocyanate groups; and
   d) mixing the prepolymer with a hydrophilic polyether polyol, a blowing agent, an end-capping agent, a reinforcing agent, and a catalyst to obtain the polyurethane foam sponge.

2. The polyurethane foam sponge according to claim 1, where in the branched triol is selected from the group consisting of 1,1,1-trimethylolpropane, triethanolamine, 1,2,4-butanetriol, glycerol, glycerol 1,2,6-hexanetriol, ethoxylate, and combinations thereof.

3. The polyurethane foam sponge according to claim 1, where in the first diisocyanate and the second diisocyanate are independently selected from the group consisting of hexamethylene diisocyanate, methylene dicyclohexyl diisocyanate, isophorone diisocyanate, and combinations thereof.

4. The polyurethane foam sponge according to claim 1, where in the hydrophobic polyether triol is selected from the group consisting of polypropylene glycol triol, poly(tetramethylene ether) glycol triol, and a combination thereof.

5. The polyurethane foam sponge according to claim 1, where in the hydrophilic polyether diol is polyethylene glycol.

6. The polyurethane foam sponge according to claim 1, where in the hydrophilic polyether polyol is polyethylene glycol having a weight-average molecular weight ranging from 400 g/mol to 2,000 g/mol.

7. The polyurethane foam sponge according to claim 1, where in the blowing agent is selected from the group consisting of water and sodium bicarbonate.

8. The polyurethane foam sponge according to claim 1, where in the end-capping agent is a silane-containing compound.

9. The polyurethane foam sponge according to claim 8, wherein the silane-containing compound is an aminosilane compound.

10. The polyurethane foam sponge according to claim 1, wherein the reinforcing agent is polysiloxane.

11. A wound dressing, comprising:
    a waterproof and vapor-permeable carrier sheet; an adhesive layer disposed on the carrier sheet; and
    a polyurethane foam sponge as claimed in claim 1, the polyurethane foam sponge being disposed on the adhesive layer opposite to the carrier sheet.

12. The wound dressing according to claim 11, where in the carrier sheet is made of polyurethane, and the adhesive layer is a polyurethane adhesive layer.

13. The wound dressing according to claim 11, which has a thickness ranging from 1 mm to 5 mm.

* * * * *